United States Patent [19]

von König et al.

[11] 4,139,387
[45] Feb. 13, 1979

[54] PROCESS FOR THE PRODUCTION OF DIRECT-POSITIVE PHOTOGRAPHIC IMAGES

[75] Inventors: Anita von König, Krefeld; Heinrich Odenwälder, Cologne; Manfred Peters; Walter Püschel, both of Leverkusen, all of Fed. Rep. of Germany

[73] Assignee: Agfa-Gevaert Aktiengesellschaft, Leverkusen, Fed. Rep. of Germany

[21] Appl. No.: 848,095

[22] Filed: Nov. 3, 1977

[30] Foreign Application Priority Data

Oct. 19, 1977 [DE] Fed. Rep. of Germany ....... 2746965

[51] Int. Cl.² ................... G03C 5/24; G03C 1/28
[52] U.S. Cl. ............................... 96/64; 96/95; 96/99; 96/107
[58] Field of Search .................. 96/64, 95, 99, 107

[56] References Cited

U.S. PATENT DOCUMENTS

| | | | |
|---|---|---|---|
| 3,227,552 | 1/1966 | Whitmore | 96/3 |
| 3,486,901 | 12/1969 | Karlson | 96/107 |
| 3,761,266 | 9/1973 | Milton | 96/107 |
| 3,977,880 | 8/1976 | Saito | 96/107 |
| 4,030,925 | 6/1977 | Leone et al. | 96/95 |

*Primary Examiner*—Won H. Louie, Jr.
*Attorney, Agent, or Firm*—Connolly and Hutz

[57] ABSTRACT

Positive images including color images are obtained by imagewise exposure and development of a material which comprises at least one light-sensitive silver halide emulsion layer which contains an unfogged direct-positive silver halide emulsion, when the development is carried out in the presence of a fogging agent of the formula

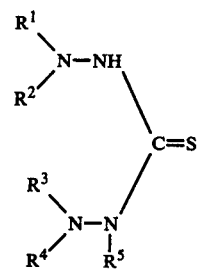

wherein the symbols are defined as hereinafter. The fogging agent is preferably contained in a layer of the material and more preferably in the unfogged direct-positive silver halide emulsion layer. For the production of color instant images the material may also contain non-diffusible color providing compounds capable in their oxidized form of being split under alkaline photographic development conditions to release diffusible dyes.

6 Claims, No Drawings

PROCESS FOR THE PRODUCTION OF DIRECT-POSITIVE PHOTOGRAPHIC IMAGES

This invention relates to a process for the production of direct positive photographic images and to a photographic material suitable for this purpose, which is developed under fogging conditions in the presence of novel fogging agents. The invention is particularly important for the production of coloured images, for example those produced by the dye diffusion transfer processes. Processes of this kind have been described, for example, in German Patent Specification No. 1,095,115 and German Offenlegungsschriften Nos. 1,930,215, 1,772,929, 1,242,762, 2,505,248 and 2,543,902.

Coloured or colour providing compounds which alter their mobility in an alkaline development medium as a result of transfer of electrons or which can be split, either in their oxidized form or their non-oxidized form, under the conditions of alkaline development to release a diffusible image dye are generally suitable for use as colour providing compounds for the dye diffusion transfer process.

Particular reference will be made in the following to a photographic material having at least one light-sensitive silver halide emulsion layer and one non-diffusible colour providing compound associated with this layer, which compound, in its oxidized form, is capable of releasing a diffusible dye in the alkaline developer medium.

Since, when using such non-diffusible colour providing compounds, the imagewise distribution of the released diffusible dyes corresponds with the silver image formed, negative colour images are obtained unless direct positive silver halide emulsions are used or a suitable reversal process is employed.

Suitable direct positive silver halide emulsions are, in principle, any of those which after imagewise exposure and a simple development, give rise to a positive silver image and to a distribution of developer oxidation products corresponding to this image. They include, for example, those silver halide emulsions in which a developable fog is produced by exposure or chemical treatment, which fog is subsequently destroyed imagewise when the emulsion is exposed imagewise under certain conditions. The fog is preserved in the unexposed areas so that, when the emulsion is finally developed, a direct positive silver image is obtained and, corresponding to this image, an imagewise distribution of diffusible dye is obtained if a colour providing compound as mentioned above was associated with the direct positive silver halide emulsion.

Particularly important for photographic dye diffusion transfer processes are the so-called unfogged direct positive silver halide emulsions which have their sensitivity to light located predominantly in the interior of the silver halide grains. When these emulsions are exposed imagewise, a latent image is formed predominantly in the interior of the silver halide grains. The development of such unfogged direct positive silver halide emulsions is carried out under fogging conditions so that a fog is produced mainly in the unexposed areas, and development produces a positive silver image. The unfogged direct positive silver halide emulsions are characterised in that when exposed samples are developed with a typical surface developer of the following composition:

| | |
|---|---|
| p-Hydroxyphenylglycine | 10 g |
| Sodium carbonate (crystallised) | 100 g |
| made up with water to | 1000 ml, | preferably no silver image or only one of very slight density is obtained whereas when an internal nuclear developer of the following composition is used:

| | |
|---|---|
| Hydroquinone | 15 g |
| N-monomethyl-p-aminophenolsulphate | 15 g |
| Sodium sulphite (anhydrous) | 50 g |
| Potassium bromide | 10 g |
| Sodium hydroxide | 25 g |
| Sodium thiosulphate (crystallised) | 20 g |
| made up with water to | 1000 ml | a silver image of sufficient density is obtained. Particularly suitable emulsions are those which, when exposed stepwise for periods ranging from 1/100 to 1 second and developed for 3 minutes at 20° C. in the internal nuclear developer described above, have a maximum density which is at least three times and preferably at least five times greater than that obtained when development of a similarly exposed material (development time 4 minutes at 20° C.) is carried out in the surface developer mentioned above.

Unfogged direct positive emulsions are, for example, those which have defects in the interior of the silver halide grains as described in U.S. Pat. No. 2,592,250 or foreign inclusions in the grains, particularly of noble metal ions, or they may be silver halide emulsions with a layered grain structure as described in German Offenlegungsschrift No. 2,308,239.

The selective fogging of unfogged direct positive emulsions which have been exposed imagewise may be carried out by treatment with a fogging agent before or during development. Reducing agents such as hydrazine or substituted hydrazines are suitable fogging agents as described, for example, in U.S. Pat. No. 3,227,552.

The compounds mentioned in said last mentioned Patent have the disadvantage that at the relatively high concentration required for fogging, they have a considerable tendency to form bubbles which distinctly impairs the optical quality of the transfer images produced. The fogging agents described in German Offenlegungsschrift No. 2,635,317 and in Research Disclosure publication No. 15 162, November 1976, are effective at much lower concentrations and therefore do not give rise to the formation of bubbles to any significant extent, but their synthesis is in part very complicated and difficult.

It is an object of the present invention to provide fogging agents for fogging unfogged direct positive silver halide emulsions, which fogging agents should be readily accessible and able to be used at such low concentrations that bubbles are not formed to any significant extent.

It has been found that thiocarbohydrazides, including those with closed rings, and the hydrazones derived from them, are excellent fogging agents for the fogging development of unfogged direct positive silver halide emulsions. These compounds correspond in one of the tautomeric forms thereof to the following formula I:

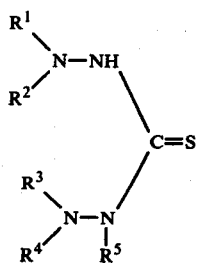

in which
R¹ and R⁴ which may be the same or different, represent hydrogen, a saturated or olefinically unsaturated aliphatic group, an aryl group, a heterocyclic group or an acyl group;

R² and R³ which may be the same or different represent hydrogen, a saturated or olefinically unsaturated aliphatic group, an aryl group or a heterocyclic group;

R⁵ represents hydrogen;

and/or

R¹ together with R² and/or

R³ together with R⁴ represent an alkylidene group, preferably a methylidene group which may be unsubstituted or substituted by alkyl, aryl, a heterocyclic group or an acyl group; two such substituents together with the carbon atom of the methylidene group may complete a carbocyclic or heterocyclic ring, for example a cyclopentane, indane, indanone, indanedione, piperidine, pyrrolidone or indolone ring. Examples of substituted methylidene groups which are not closed to form a ring include ethylidene, 3,3-dimethyl-2-butylidene, benzylidene and furfurylidene;

and/or

R¹ together with R⁴ or R⁵ represent the group required for completing a 5- or 6-membered heterocyclic ring, in particular a 1,2,3,4-tetrazolidine-5-thione ring, a hexahydro-1,2,4,5-tetrazine-3-thione ring, a hexahydro-1,2,4-triazine-3-thione ring or a 2,3,4,5-tetrahydro-1,2,4-triazine-3-thione ring; this completing group is generally a methylene group which may itself be monosubstituted or disubstituted, e.g. with alkyl, cycloalkyl, aralkyl or aryl; two such substituents, e.g. two alkyl groups, may form a ring together with the carbon atom of the methylene group, in particular a carbocyclic ring, for example a cyclopentane, cyclohexane, 3,3,5-trimethylcyclohexane, cyclododecane, indane or tetraline ring or a heterocyclic ring such as a piperidine ring.

According to a preferred embodiment at least one of R¹ and R⁴ is hydrogen.

Examples of saturated aliphatic groups include alkyl groups, which may be straight or branched chain or cyclic and may contain up to 18 carbon atoms and may in turn be substituted, for example with carboxyl, carbamoyl or nitrile.

An example of an olefinically unsaturated aliphatic group is allyl.

The aryl group may in particular be phenyl, which may be substituted, for example by halogen, hydroxyl, alkoxy, alkylthio, carboxyl, sulphamoyl, amino and/or alkyl.

By acyl groups are meant groups which are derived from aliphatic or aromatic carboxylic or sulphonic acids, including (thio)carbonic acid monoesters, carbamic acids and sulphamic acids. Examples of such acyl groups include formyl, acetyl, benzoyl, phenylsulphonyl, carbamoyl, phenylcarbamoyl, ethoxycarbonyl and ethoxythiocarbonyl.

The present invention thus relates to a process for the production of direct-positive photographic images, in which process a photographic recording material having at least one light-sensitive silver halide emulsion layer containing an unfogged direct-positive silver halide emulsion is exposed imagewise and developed in the presence of a fogging agent, characterised in that the fogging agent used is a compound of the general formula I.

The invention also relates to a photographic recording material having at least one light-sensitive silver halide emulsion layer which contains an unfogged direct-positive silver halide emulsion which material contains a compound of the general formula I in one or more of its layers. The fogging agent of the present invention is preferably situated in a light-sensitive layer which contains an unfogged direct-positive silver halide emulsion.

Examples of compounds of the general formula I are shown below (several of the compounds have not a definite melting point, but are decomposed on heating in this case the temperature of decomposition (dec.) is given instead of the melting point (m.p.):

Table $$R^6-NH-NH-\overset{\overset{S}{\|}}{C}-NH-NH-R^7$$

| Compound No. | R⁶ | R⁷ | |
|---|---|---|---|
| 1 | —H | —H | 168° C dec. |
| 2 | —C(O)—NH₂ | —C(O)—NH₂ | 217° C dec. |
| 3 | —H | —C(S)—OC₂H₅ | 187° C dec. (Hydrochlorid) |
| 4 | —C(O)—NH—C₆H₅ | —C(O)—NH—C₆H₅ | 225° C dec. |

Table-continued

| # | Structure 1 | Structure 2 | Temp |
|---|---|---|---|
| 5 | -C(=O)-NH-(2-methylphenyl) | -C(=O)-NH-(2-methylphenyl) | 208° C dec. |
| 6 | -SO$_2$-(4-methylphenyl) | -SO$_2$-(4-methylphenyl) | 184° C dec. |
| 7 | -phenyl | -phenyl | 152° C dec. |

$$R^6-NH-NH-\overset{\overset{S}{\|}}{C}-NH-N=\begin{matrix}R^8\\R^8\end{matrix}$$

| # | R$^6$ | R$^8$ | Temp |
|---|---|---|---|
| 8 | —H | =C(CH$_3$)–phenyl | 171° C dec. |
| 9 | —H | =CH–(furyl) | 186° C dec. |
| 10 | —H | =CH–(4-hydroxyphenyl) | 218° C dec. |
| 11 | —H | =CH–(4-N,N-dimethylaminophenyl) | 194° C dec. |
| 12 | —H | =CH–(3-hydroxyphenyl) | 180° C dec. |
| 13 | —H | =(1-butyl-5-oxo-pyrrolidinyl-2-COOC$_2$H$_5$) | 173° C dec. |
| 14 | —H | =C(CH$_3$)–C(CH$_3$)$_3$ | 140–142° C mp. |
| 15 | —H | =CH–phenyl | 193° C |
| 16 | —H | =CH–(5-sulfo-furyl) | 222° C dec. |
| 17 | -C(=O)-NH- | =CH–(furyl) | 186° C dec. |
| 18 | H | =(3,4-dihydronaphthalen-1-yl) | 165° C dec. |

Table-continued

| No. | | | |
|---|---|---|---|
| 19 | H | =C(CH₃)-C₆H₄-S-C₁₂H₂₅ (para) | 157° C–159° C mp. |
| 20 | H | =C(C₃H₇)(C₃H₇) | 147° C–148° C mp. |
| 21 | H | =C(CH₃)-C₆H₄-OH (para) | 225° C dec. |
| 22 | H | =C(C₂H₅)-CH₂-CH(CH₃)-CH₂-CH₃ | 99–100° C mp |

| Compound No. | R⁹ | R⁸ | |
|---|---|---|---|
| | \multicolumn{3}{c}{$R^9=N-NH-\overset{O}{\overset{\|}{C}}-NH-N=R^8$} | |
| 23 | =CH-C₆H₄-OH | =CH-C₆H₄-OH | 209° C dec. |

Structure with R¹⁰ on spiro carbon bearing two NH-NH groups connected to C=S:

| No. | R¹⁰ | mp |
|---|---|---|
| 24 | cyclopentane (spiro) | 184° C dec. |
| 25 | cyclododecane (spiro) | 200° C dec. |
| 26 | 3,3,5-trimethylcyclohexane (spiro) | 202° C dec. |
| 27 | 2,2-disubstituted indane | 192° C dec. |
| 28 | cyclohexane (spiro) | 170° C. dec. |
| 29 | N-methylpiperidine (spiro) | 206° C dec. |

Table-continued $$R^{11}\underset{R^{12}}{\overset{NH-NH}{>}}\underset{NH-NH}{\overset{}{>}}C=S$$

| | $R^{11}$ | $R^{12}$ | |
|---|---|---|---|
| 30 | —CH$_3$ | —C$_9$H$_{19}$ | 146° C dec. |
| 31 | —H | —CH(CH$_3$)$_2$ (—CH with two CH$_3$) | 159.5–161° C dec. |
| 32 | ohne Strukturformel | C$_{13}$H$_{28}$N$_4$O$_{11}$S | 157° C dec. |
| 33 | —CH$_3$ | —CH$_3$ | 210–211° C dec. |
| 34 | —(phenyl) | —CH(OH)—(phenyl) | 157–160° C dec. |
| 35 | —H | —(cyclohexyl, H) | 167–169° C dec. |

36

(cyclohexyl)
$$\underset{NH}{\overset{NH-NH}{>}}C=S,\ C\underset{\|}{\overset{}{=}}N-NH_2$$

172° C dec.

37

$$\underset{CH_3}{\overset{CH_3}{>}}\underset{NH}{\overset{NH-NH}{>}}C=S,\ C\underset{\|}{\overset{}{=}}N-NH_2$$

198° C dec.

Preparation of the compounds according to the invention is for the most part carried out by methods known in the literature. The preparation of compound 4, for example, has been described in J. Indian Chem. Soc. 1, 141 and that of compounds 14, 15, 28 and 33 in J. Org. Chem. 34, 756. Bisthiocarbohydrazones, such as compound 23, for example, may be obtained directly from thiocarbohydrazide or from the monothiocarbohydrazone by reaction with the corresponding carbonyl compound. The last mentioned method may also be used to obtain asymmetric bis-thiocarbohydrazones, and the monothiocarbohydrazone used in the process may also be present in the cyclic hexahydro-1,2,4,5-tetrazine-3-thio form (see compound 24).

Isolation of the compounds according to the invention may be dispensed with in suitable cases, especially if the components react together sufficiently rapidly and do not give rise to undesirable by-products. This method may be used to advantage if isolation of the reaction product is accompanied by a considerable loss in yield. For example, instead of compound 32, the appropriate reaction mixture may be used for the purpose of the invention.

The monohydrazones of thiocarbohydrazide may also contain a cyclic structure in addition to the open chain structure as described by R. W. Lamon in J.Org. Chem. 34 (1969) 756. It is therefore possible that under certain conditions the compound of formula 9, for example, may be partly or completely in the form of the cyclic structure while the compound of formula 24, for example, may be partly or completely in the form of the open chain structure.

Preparation of Compound 3

42 g of diaminoguanidine hydrochloride are dissolved in 300 ml of water, and 53 g of sodium xanthogenate are added after the pH of the solution has been adjusted to 7 with sodium hydroxide. The yellow product which precipitates when the mixture is left to stand overnight is suction filtered and purified by redissolving it from alcohol and hydrochloric acid. The yield is 31 g, with a point of decomposition of 187° C.

Preparation of Compound 6

38.2 g of p-toluenesulphochloride are added portionwise to 10.6 g of thiocarbohydrazide in 120 ml of pyridine over a period of 30 minutes with stirring. After a further 2 hours, the reaction product is precipitated with water and the precipitate formed is suction filtered and recrystallised once from methanol/water. 39 g of 1,5-bis-(4-toluenesulphonyl)-thiocarbohydrazide of decomposition point 182°–184° C. are obtained.

Preparation of Compound 32

20 g of glucose are dissolved in 40 ml of water to which 0.5 ml of glacial acetic acid has previously been added. After the addition of 5 g of thiocarbohydrazide, the reaction mixture is heated to 50° C. with stirring. It dissolves after a short time. After a further 30 minutes' stirring at 50° C. and 2 hours at room temperature, 40 ml of n-propanol are added. After a further 2 hours, the resulting precipitate is suction filtered, washed with 40 ml of n-propanol and finally mixed with 90 ml of ethyl acetate, suction filtered and dried in air. 11.8 g of a product having the overall composition $C_{18}H_{28}N_4O_{11}S$ are obtained; the product sinters at 145° C. and is decomposed at 157° C.; according to the UV-spectrum ($\lambda_{max}$ = 238 nm, $\epsilon$ = 12.6 × 10$^3$) it is present as the thiocarbohydrazone in the cyclic form.

Compounds 36 and 37 are prepared by reacting the corresponding ketones with thiocarbohydrazide in the presence of nascent hydrogen cyanide. The cyanogen derivatives obtained are subsequently cyclised with hydrochloric acid as described in German Offenlegungsschrift No. 2,000,622.

The compounds represented by the general formula I are suitable fogging agents (nucleating agents) for the fogging development of unfogged direct-positive silver halide emulsions. For this purpose, they are generally incorporated directly into the silver halide emulsion layer but they may also be added to a light-insensitive layer of binder adjacent to the silver halide emulsion layer or to the alkaline processing liquid. Compounds of the general formula I in many cases prove to be superior to the known fogging agents such as acetylphenylhydrazine since they are effective at much lower concentrations, e.g. at 0.1 mg to 100 mg per mol of silver halide, and have no tendency to form bubbles.

The compounds according to the present invention are at least as effective as the acyl hydrazino phenylthioureas according to German Offenlegungsschrift No. 2,635,317 and they have the special advantage over these compounds of being readily accessible. In most cases thiocarbohydrazide which itself is readily available from the raw materials $CS_2$ and hydrazine hydrate (J.prakt.Chem.[2] 132, 222 (1932)) is used as starting compound and is reacted with a ketone, an aldehyde or an acylating agent such as a carboxylic acid chloride or an isocyanate.

When unfogged direct-positive silver halide emulsion layers are developed in the presence of compounds according to the present invention, silver image is formed predominantly in the unexposed areas while the exposed areas are developed only to a minimal density (fog). The unfogged direct-positive silver halide emulsions are generally of the kind which are capable of producing a latent image in the interior of the silver halide grains on exposure.

The required high internal grain sensitivity in the emulsions used, which is produced by centres in the interior of the grain which promote the formation of photolytic silver, can be achieved by various means. It has been found to be particularly suitable to use silver halide emulsions which have grains with a layered grain structure consisting of silver halide phases containing differing amounts of different silver halides.

The internal grain sensitivity is determined by the properties of the phase interfaces or transitions between the phases which consist of different silver halides. Emulsions of this kind have been described, for example, in German Offenlegungsschriften Nos. 2,308,239 and 2,332,802.

Silver halide emulsions which have foreign inclusions in their silver halide grains are also suitable. These emulsions generally have a layered grain structure. They may be prepared by first preparing a fine grained silver halide emulsion whose grains form the nuclei for the finished emulsion. This starting emulsion may be chemically or physically modified on the surface. A shell of the same or a different silver halide is then precipitated on these grains. The preparation of such emulsions has been described, e.g. in German Patent Specification No. 1,169,290. Reference may also be made to U.S. Pat. Nos. 3,206,313; 3,317,322 and 3,367,778. In the case of the last mentioned Patent Specification, the surface is not fogged. Other suitable processes have been described in U.S. Pat. Nos. 3,447,927; 3,531,291 and 3,271,157 and in British Pat. Nos. 1,027,146 and 1,151,782. The aforesaid foreign inclusions may be either foreign metal ions of different valencies or noble metal nuclei, e.g. of silver, gold, platinum, palladium or iridium, or nuclei formed by reaction with labile sulphur compounds. The silver halide emulsions used according to the invention may also be prepared by precipitating the silver halide grains in the presence of foreign metal ions, in particular polyvalent metal ions. This can be done, for example, by adding aqueous solutions of salts of the particular metal during precipitation. Suitable salts for this purpose are, for example, salts of divalent lead or trivalent antimony, bismuth, arsenic, gold, iridium or rhodium and salts of tetravalent platinum or iridium. The concentration of foreign inclusions may vary within wide limits but concentrations of the order of at least $10^{-7}$ to $10^{-5}$ mol-%, based on the total quantity of silver halide of the grain, are generally sufficient.

The silver halide emulsions to be used according to the invention are prepared by the known methods used for preparing silver halide emulsions with a layered grain structure. Double inflow processes in which the pAg and pH are kept at certain levels are preferred. Emulsions with a layered grain structure and processes for their preparation have been described in German Patent Specification No. 1,169,290 and British Pat. No. 1,027,146. Reference may also be made to the publication by E. Moisar and S. Wagner in "Berichte der Bunsengesellschaft für physikalische Chemie" 67 (1963), pages 356–359, and P. Claes and R. Berendsen in "Photographische Korrespondenz" 101 (1965), pages 37–42. The pAg-values to be adjusted during precipitation may be continuously measured electrometrically so that the rate of inflow of the precipitation components can be controlled according to the values measured.

Both homodisperse and heterodisperse silver halide emulsions are suitable for the material according to the invention. By heterodisperse silver halide emulsions are meant emulsions having a grain size distribution such that preferably at least 10% and most preferably at least 20% by weight of the silver halide grains have a diameter which deviates by at least 40% from the average grain diameter.

The silver halide grains are mainly irregular in form. The absolute value of the average grain size may vary within wide limits. Both fine grained heterodisperse silver halide emulsions with an average diameter of below 0.5 μm, preferably below 0.3 μm and coarse grained heterodisperse emulsions with an average grain size of between 0.5 and 4 μm may be used, depending on the purpose for which the photographic material is intended.

Homodisperse silver halide emulsions with a narrow grain size distribution are also suitable for the material according to the invention. Preferably, about 95% by weight of the silver halide grains have a diameter which differs by not more than 40%, preferably by not more than 30% from the average grain diameter. The silver halide grains of the homodisperse silver halide emulsions may have any known shapes, e.g. they may be cubical or octahedric or they may have a tetradecahedric mixed form.

The absolute value of the average grain size may vary within wide limits. Both fine grained monodisperse silver halide emulsions with an average diameter of less than 0.5 μm, preferably less than 0.3 μm, and coarse grained monodisperse emulsions with an average grain size of between 0.5 and 2 μm may be used, depending on the purpose for which the photographic material is intended.

The protective colloid or binder used for the silver halide emulsion layer may be any of the usual hydrophilic film forming substances, e.g. proteins, in particular gelatine, alginic acid or its derivatives such as its esters, amides or salts, cellulose derivatives such as carboxymethylcellulose and cellulose sulphates, starch or its derivatives or hydrophilic synthetic binders such as polyvinyl alcohol, partially saponified polyvinyl acetate and polyvinylpyrrolidone. The hydrophilic binders in the layers may also be mixed with solutions or dispersions of other synthetic binders such as homopolymers or copolymers of acrylic or methacrylic acid or their derivatives such as esters, amides or nitriles, or vinyl polymers such as vinyl esters or ethers.

The silver halide emulsions used according to the invention may contain the usual emulsion additives, provided that the surface sensitivity is kept as low as possible.

The emulsions may also be spectrally sensitized. Suitable sensitizers for this purpose include, for example, the usual monomethine or polymethine dyes such as acid or basic cyanines, hemicyanines, streptocyanines, merocyanines, oxonoles, hemioxonoles, styryl dyes or the like and trinuclear or higher nuclear methine dyes, for example, rhodacyanines or neocyanines. Sensitizers of this kind have been described, for example, in the work by F. M. Hamer "The Cyanine Dyes and Related Compounds" (1964), Interscience Publishers John Wiley and Sons.

In addition to containing the compounds according to the invention, the emulsions may contain the usual stabilizers, e.g. homopolar compounds or salts of mercury having aromatic or heterocyclic rings, such as mercapto triazoles, or simple mercury salts, sulphonium mercury double salts and other mercury compounds. Azaindenes are also suitable stabilizers, particularly tetra- and penta-azaindenes and especially those which are substituted with hydroxyl or amino groups. Compounds of this type have been described in the article by Birr, Z.Wiss. Phot 47, 2 to 27 (1952). Other suitable stabilizers include heterocyclic mercapto compounds, e.g. phenylmercaptotetrazole, quaternary benzothiazole derivatives and benzotriazoles.

The emulsions may be hardened in the usual manner, for example with formaldehyde or halogen-substituted aldehydes containing a carboxyl group, such as mucobromic acids, diketones, methasulphonic acid esters, dialdehydes, carbodiimides, carbamoylpyridinium salts and carbamoyl oxypyridinium salts.

The photographic recording material according to the present invention contains at least one but as a rule at least three different light-sensitive, unfogged directpositive silver halide emulsion layers, one of which is sensitive to blue light, another to green light and a third to red light. With each of these layers a non-diffusible colour providing compound is associated from which diffusible dyes or dye precursors are released by development so as to produce a partial colour image of a colour which is generally complementary to the colour of that light to which the associated silver halide emulsion layer is predominantly sensitive.

By "association" and "associated" is meant that the silver halide emulsions and the non-diffusible colour providing compound are so arranged in relation to each other that an interaction between them can take place to produce an imagewise correspondence between the silver image formed and the distribution of the released diffusible dye. The associated colour providing compound may be incorporated in a layer adjacent to the silver halide emulsion layer and this adjacent layer is preferably situated behind the silver halide emulsion layer (viewed in the direction of the incident light used for exposure).

The non-diffusible colour providing compounds must contain a residue of a performed dye or of a dye precursor, e.g. of a coupler, which is released as a diffusible dye as a result of development and is then capable of diffusing into the image-receiving layer which is in contact with the light-sensitive element containing the light-sensitive silver halide emulsion layers and colour providing compounds. The colour providing compounds therefore generally contain a dye residue and a residue which confers diffusion resistance, the two residues being linked together by certain atomic groupings forming a linkage which can be dissolved by development. Such non-diffusible, colour providing compounds containing a preformed dye residue have already been described in various writings. Examples of suitable compounds which have been mentioned in the literature include those among the diffusible dye couplers according to German Pat. No. 1,095,115 which contain a preformed dye residue; the hydrazone compounds according to German Pat. No. 1,930,215; those of the hydrazine compounds of German Offenlegungsschrift No. 2,228,361 which are non-diffusible; and the colour providing compound mentioned in German Offenlegungsschriften Nos. 1,772,929; 2,242,762; 2,406,664 and 2,505,248 and in German patent applications Nos. P 26 45 656.4, P 26 52 463.0 and P 26 52 316.0. In some cases, the dye may only be formed during development as described in German Pat. No. 1,095,115. In the description which follows, the term "dye residues" will also be used to cover residues of dye precursor compounds, e.g. of colour couplers.

The dye residues may be taken from all classes of dyes, provided they are sufficiently diffusible to be able to diffuse through the layers of the light-sensitive material to reach the image receiving layer. On account of this requirement, the dye residues preferably have one or more water-solubilizing groups. The following groups, among others, are suitable for this purpose: Carboxyl groups, sulpho groups and aliphatic and phenolic hydroxyl groups. The following are examples of dyes which are particularly suitable for the process according to the invention: Azo dyes, azomethine dyes, anthraquinone dyes, phthalocyanine dyes, indigoid dyes and triphenylmethane dyes. The dye residue may already contain the number of solubilizing groups necessary for rendering it sufficiently diffusible, but occasionally it is particularly advantageous if a solubilizing group which is originally present in a latent form and remains with the dye residue comes into operation when the dye is released and thereby imparts an additional capacity for diffusion to the dye residue. Such cases have been described, for example, in German Offenlegungsschriften Nos. 1,930,215 and 2,406,664.

The colour providing compounds should not diffuse in the layers. They are therefore provided with groups which confer diffusion resistance. The groups used for this purpose are preferably organic groups, which may generally contain straight or branched chain aliphatic groups and may also contain carbocyclic or heterocyclic aromatic groups. The aliphatic portion of these groups generally contains from 8 to 20 carbon atoms. These groups are attached to the remainder of the molecule either directly or indirectly, e.g. through one of the following groups: —O—, —S—, —CO—, —SO$_2$—, —NR—, —CONR— or —SO$_2$NR, in which R represents hydrogen or alkyl.

For carrying out the dye diffusion transfer process according to the present invention, there are used a light-sensitive element which contains the direct positive silver halide emulsion layers and non-diffusible colour providing compounds and an image receiving element in which the desired colour image is produced by the diffusible dyes which are transferred to it imagewise. In order to achieve this diffusion, firm contact must be established between the light-sensitive element and image receiving element for at least a finite period of time during the development time in order that the imagewise distribution of diffusible dyes produced in the light-sensitive element as a result of development may be transferred to the image receiving element. This contact may be established after development has started or it may already be established before the onset of development. The latter is the case if, for example, a material in which the light-sensitive element and image receiving element form an integral unit is used for carrying out the dye diffusion transfer process. The present invention is preferably concerned with those forms of the dye diffusion transfer process in which such an integral unit, hereinafter referred to as monosheet material, is preserved even after completion of the development process, i.e. the light-sensitive element is not separated from the image receptor element even after the dye has been transferred. One such arrangement has been described, for example, in German Offenlegungsschrift No. 2,019,430.

A light-sensitive material suitable for carrying out the dye diffusion transfer process according to the present invention may have, for example, the following layer elements:

(1) a transparent layer substrate
(2) an image-receiving layer
(3) a light impervious layer
(4) a light-sensitive element comprising at least one light-sensitive, unfogged direct-positive silver halide emulsion layer and at least one non-diffusible colour providing compound
(5) a retarding layer
(6) an acid polymer layer
(7) a transparent layer substrate.

To produce the monosheet material, two different parts may be prepared separately, i.e. the light-sensitive part (layer elements 1 to 4) and the cover sheet (layer elements 5 to 7), and the two parts may then be placed face to face with their active surfaces in contact and bonded together, optionally with the interposition of spacer strips so that space is left between the two parts for an accurately calculated quantity of processing liquid. The layer elements 5 and 6, which together form the neutralisation system, may also be arranged between the layer substrate and the image receiving layer of the light-sensitive part, either in addition to or instead of being placed in the first mentioned position, although in that case they would be arranged in the opposite sequence of layers.

The fogging agents of the present invention are preferably located in the light-sensitive element and more preferably in a light-sensitive unfogged direct-positive silver halide emulsion layer.

Means are provided for introducing a processing liquid between the light-sensitive part and the cover sheet, e.g. in the form of a rupturable container which is arranged at the side and which pours its contents between two adjacent layers of the monosheet material when mechanical force is applied.

The processing liquid is a liquid, viscous or pasty alkaline mass which releases the development of the exposed silver halide. The auxiliary substances required for developing the silver halide may be contained in the processing mass but they may also be accommodated in one or more layers of the photographic material, for example in one or more layers of the light-sensitive element or in a separate layer of binder, for example on the cover sheet.

The processing liquid may also contain other reagents such as stabilizers, antioxidants, opacifying agents and viscosity increasing additives. The following viscosity increasing substances, for example, may be added to the processing mass: Cellulose derivatives, for example carboxyalkylcellulose, hydroxyethylcellulose, starch and polyvinyl alcohol. The fogging agents of the present invention may also be partly or completely contained in the processing liquid.

Although the fogging agents of the present invention are of particular significance for instant colour photography, their use is not restricted to this field. They may be used to equal advantage for the production of positive colour images by the conventional chromogenic development process or for the production of direct-positive silver images (black-and-white). In the latter case, the use of colour providing compounds is unnecessary. If coloured images are to be produced by the conventional chromogenic development process the various direct-positive silver halide emulsion layers of differing spectral sensitivities are associated, not with non-diffusible colour providing compounds, but with non-diffusible colour couplers from which non-diffusible dyes are produced by development with the usual colour developers, e.g. those based on p-phenylene diamine, the absorption range of these dyes generally corresponding to the range of sensitivity of the associated silver halide emulsion layer.

The invention will now be further described with reference to the following Examples:

EXAMPLES OF PRACTICAL APPLICATION 1–4

A light-sensitive element of a photographic material according to the invention was prepared by applying the following layers in succession to a transparent polyester foil used as substrate. The quantities given are based in each case on 1 m$^2$.

1. A layer of mordant consisting of 5.7 g of a polyurethane of 4,4-diphenyldiisocyanate, N-ethyl-diethanolamine and epichlorohydrin (corresponding to German Patent Application P 26 31 529.9) and 5.0 g of gelatine;

2. a white pigment layer of 24 g of titanium dioxide and 2.4 g of gelatine;

3. a black pigment layer of 1.9 g of carbon black and 2g of gelatine;

4. a dye layer (cyan) of 0.53 g of compound A (milled in a sandmill) and 1 g of gelatine;

5. a red sensitized emulsion layer containing a silver bromide internal grain emulsion which has been ripened on the surface and functions as a direct positive emulsion, silver application 1.27 g, gelatine application 1.27 g, the emulsion layer also containing 0.2 g of the potassium salt of octadecyl hydroquinone sulphonic acid and the appropriate fogging agent which is indicated in Table 1 for Examples 1-4;

6. A barrier layer of 1 g of the potassium salt of octadecyl hydroquinone sulphonic acid and 1 g of gelatine;

7. a dye layer (magenta) of 0.53 g of compound B (milled in a sandmill) and 1 g of gelatine;

8. A green sensitized emulsion layer with a surface-ripened direct positively functioning silver bromide internal grain emulsion, silver application 1.27 g, gelatine application 1.27 g, and with 0.2 g of the potassium salt of octadecyl hydroquinone sulphonic acid and the appropriate fogging agent indicated in Table 1 for Examples 1-4;

9. a barrier layer identical to layer 6;

10. a dye layer (yellow) of 1.06 g of compound C (milled in a sandmill) and 1.06 g of gelatine;

11. a blue sensitized emulsion layer containing a surface-ripened, direct positively functioning silver bromide internal grain emulsion, silver application 1.27 g, gelatine application 1.27 g, with 0.2 g of the potassium salt of octadecyl hydroquinone sulphonic acid and the appropriate fogging agent indicated in Table 1 for Examples 1-4;

12. A covering layer of 0.8 g of gelatine and 0.8 g of a carbodiimide instant hardener of formula E.

The light-sensitive materials were developed with a paste of the following composition:

1.5 ml benzyl alcohol
30 g hydroxyethylcellulose (Nastrosol HHR 250)
56 g potassium hydroxide
1 g sodium sulphite
2.75 g 5-methyl-benzotriazole
8 g 4-hydroxymethyl-4-methylphenidone
0.2 g hydroquinone
made up with water to 1000 ml.

A cover sheet of polyester comprising the following layers was prepared for neutralising the material of the image after development:

1. An acid polymer layer of 20 g of a copolymer of acrylic acid and ethyl acrylate (70/30), 2. a retarding layer of 5.2 g of a mixture of cellulosediacetate and styromal (94/6), 3. A second retarding layer of 0.8 g of a latex consisting of a copolymer of 71 parts of vinylidene chloride, 26 parts of methyl methacrylate and 3 parts of itaconic acid.

After imagewise exposure, a sheet of the light-sensitive element was covered with a sheet of the neutralisation system with interposition of two spacer strips placed laterally, and a rupturable container for developer paste was placed at one end of the set formed in this way. The film set was passed through a pair of squeezing rollers so that the developer paste was distributed between the light-sensitive element and the neutralisation element. The thickness of the layer of paste was 110μ. A positive image of the original was visable through the polyester substrate on the titanium dioxide layer which served as image background. The maximum density and the whites (fog) were measured after one hour. It could be assumed with certainty that by the end of this time, the lowering of pH by the neutralisation system had been completed. The results are summarized in Table 1.

EXAMPLES OF PRACTICAL APPLICATION 5 and 6

The following layers were applied to the arrangement of layers 1 to 3 described in Examples 1 to 4. The quantities indicated are based in each case on 1 m².

4. A dye layer (cyan) of 0.53 g of compound A emulsified in tricresyl phosphate, and 1 g of gelatine;

5. a red sensitized emulsion layer containing a surface-ripened, direct positively functioning silver bromide internal grain emulsion, silver application 1.27 g and gelatine application 1.27 g, with 0.2 g of the potassium salt of octadecyl hydroquinone sulphonic acid and the appropriate fogging agent, indicated in Table 1 under the examples numbers 5 and 6;

6. A barrier layer of 1 g of the potassium salt of octadecyl hydroquinone sulphonic acid and 1 g of gelatine;

7. a dye layer (magenta) of 0.88 g of compound B emulsified in tricresyl phosphate, and 1 g of gelatine;

8. a green sensitized emulsion layer containing a surface ripened, direct positively functioning silver bromide internal grain emulsion, silver application 1.8 g, gelatine application 1.8 g, with 0.28 g of the potassium salt of octadecyl hydroquinone sulphonic acid and the appropriate fogging agent, indicated in Table 1 under the example numbers 5 and 6;

9. a barrier layer identical to layer 6;

10. a dye layer (yellow) of 1.06 g of compound C emulsified in tricresyl phosphate, and 1.06 g of gelatine;

11. A blue sensitized emulsion layer containing a surface ripened, direct positively functioning silver bromide internal grain emulsion, silver application 1.27 g, gelatine application 1.27 g, with 0.2 g of the potassium salt of octadecyl hydroquinone sulphonic acid and the appropriate fogging agent, indicated in Table 1 under the example numbers 5 and 6;

12. a protective layer of 0.1 g of the potassium salt of octadecyl hydroquinone sulphonic acid and 1 g of gelatine;

13. a covering layer of 0.8 g of gelatine and 0.4 g of a carbodiimide instant hardener of formula E.

The material was processed and the result interpreted as described in Examples 1 to 4. The results are summarized in Table 1.

As can be seen from Table 1, the effective quantity of the fogging agent claimed according to the invention is distinctly lower than that of conventional fogging agents, for example acetylphenylhydrazine fogging agents. Due to the low concentration, no bubbles could be seen to be formed in the fogging agents claimed whereas in the case of less effective acetylphenylhydrazine fogging agents, which must be used at higher concentrations, such bubbles often cause significant interference.

Table 1

| Example No. | mg of fogging agent per mol of silver halide | | min / max yellow magenta cyan |
|---|---|---|---|
| 1 | 350 | mg acetylphenylhydrazine (comparison substance) | 0.36 / 1.91 0.24 / 2.30 |

Table 1-continued

| Example No. | mg of fogging agent per mol of silver halide | | min / max yellow magenta cyan |
|---|---|---|---|
| | " | | 0.23 / 1.85 |
| 2 | 70 | mg acetylphenylhydrazine (comparison substance) | 0.28 / 1.50 |
| | " | | 0.23 / 1.36 |
| | " | | 0.20 / 1.55 |
| 3 | 0.14 | mg Compound 31 | 0.28 / 1.66 |
| | " | | 0.25 / 1.97 |
| | " | | 0.20 / 1.65 |
| 4 | 1.4 | mg Compound 24 | 0.33 / 1.87 |
| | " | | 0.30 / 2.20 |
| | " | | 0.26 / 1.92 |
| 5 | 1.5 | mg Compound 36 | 0.41 / 1.75 |
| | " | | 0.39 / 1.89 |
| | " | | 0.42 / 1.77 |
| 6 | 11.5 | mg Compound 18 | 0.41 / 1.80 |
| | | | 0.39 / 1.91 |
| | | | 0.42 / 1.91 |

EXAMPLES OF PRACTICAL APPLICATION 7 and 8

Using the same arrangement of layers as in Examples 1 to 4, compound No. 32 (Example 8) was used as fogging agent in layers 5, 8 and 11 and 1-p-formyl-hydrazinophenyl-3-phenyl-2-thiourea (Example 7) was used as comparison substance. The results are summarised in Table 2.

Table 2

| Example No. | mg of fogging agent per mol of silver halide | min / max |
|---|---|---|
| 7 | 1.4 of 1-p-formyl-hydrazino-phenyl-3-phenyl-2-thiourea (comparison substance) | 0.30 / 1.74 |
| | | 0.29 / 2.16 |
| | | 0.24 / 1.84 |
| 8 | 1.4 mg of compound 32 | 0.31 / 1.84 |
| | | 0.27 / 2.27 |
| | | 0.23 / 1.96 |

When compound 32, for example, was compared with a known fogging agent which adsorbs on the silver halide grain, the compound 1-p-formyl-hydrazinophenyl-3-phenyl-2-thiourea, it was found that compound 32 provides at least equally favourable results and even tends to be more highly active. One special advantage of compound 32 is that in contrast to the compound of Example 7 (barely soluble in water) it can be poured from the aqueous phase which ensures problem-free casting. There is no damage, e.g. to dye emulsions, by flocculation, agglomeration, crystallisation, etc. due to having to use water-miscible organic solvents, and no trouble due to sedimentation of the silver halides caused by reduction in the viscosity of casting solutions when large quantities of solvents are used.

EXAMPLES OF PRACTICAL APPLICATION 9–31

Using the same arrangement of layers 1 to 3 as described in Examples 1 to 4, the following layers were applied. The quantities given are based on 1 m².

4. A dye layer (magenta) of 0.96 g of compound D, 40 mg of octadecylhydroquinone sulphonic acid and 0.96 g of gelatine;

5. A green sensitized emulsion layer with a direct positively functioning silver chlorobromide internal grain emulsion which has not been ripened on the surface, silver application 1.66 g, with 1.3 mg of 1-(3'-carboxyphenyl)-5-mercaptotetrazole, 66 mg of octadecylhydroquinone sulphonic acid, 1.2 g of gelatine and the fogging agents indicated in Table 3;

6. a protective layer of 2.6 g of gelatine.

A strip of the light-sensitive element was exposed through a step wedge. After application of a rupturable container for developer paste at one end and two spacer strips 180μ in thickness at the two sides of the light-sensitive element, the element was covered with a polyester foil. The set formed in this way was passed through a pair of squeezing rollers so that the developer paste was distributed between the light-sensitive element and the cover sheet. A paste of the following composition was used as developer:

40 g potassium hydroxide
10 ml benzyl alcohol
1 g paraformaldehyde
3 g 5-methyl-benzotriazole
0.25 g ascorbic acid
0.1 g hydroquinone
1.3 g 4-hydroxymethyl-4-methyl-phenidone
30 g hydroxyethylcellulose, Natrosol HHR 250
made up with water to 1000 ml.

After a development time of 10 minutes, the image element was separated off, neutralised in a 3% acetic acid bath and washed to free it from any paste adhering to it. A positive magenta image could be seen through the transparent substrate, with the titanium dioxide layer serving as image background.

The $D_{min}/D_{max}$ values were determined, based on acetylphenylhydrazine as comparison substance, taking the values for acetylphenylhydrazine as 100/100. The results are summarised in Table 3.

Table 3

| Example No. | Fogging agent Compound No. | mg silver halide | $D_{min}/D_{max}$ standardised |
|---|---|---|---|
| 9 | Acetylphenylhydrazine (Comparison substance) | 850 | 100 / 100 (0.31 / 1.83) |
| 10 | " | 425 | 107 / 71 |
| 11 | " | 170 | 75 / 28 |
| 12 | 1 | 0.17 | 110 / 95 |
| 13 | 2 | 1.7 | 106 / 104 |
| 14 | 4 | 4.2 | 106/104 |
| 15 | 5 | 5.1 | 106 / 106 |
| 16 | 10 | 34.0 | 128 / 83 |
| 17 | 11 | 25.5 | 118 / 101 |
| 18 | 12 | 8.5 | 109 / 94 |
| 19 | 15 | 25.5 | 105 / 118 |
| 20 | 16 | 34.0 | 104 / 89 |
| 21 | 20 | 1.7 | 100 / 102 |
| 22 | 21 | 17.0 | 105 / 92 |
| 23 | 22 | 20.4 | 95 / 95 |
| 24 | 23 | 127.0 | 119 / 92 |
| 25 | 25 | 8.5 | 97 / 92 |
| 26 | 27 | 1.7 | 139 / 97 |
| 27 | 28 | 4.2 | 94 / 107 |
| 28 | 29 | 3.4 | 92 / 93 |
| 29 | 30 | 8.5 | 100 / 106 |
| 30 | 33 | 5.1 | 130 / 108 |
| 31 | 37 | 68.0 | 123 / 104 |

The distinctly superior activity of the fogging agents given in these examples is clear from a comparison with a conventional fogging agent of the acetylphenylhydrazine series.

Annex of the formulae of the examples

-continued
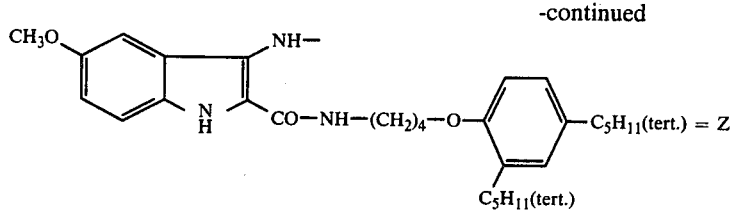
Compound A (blue-green)
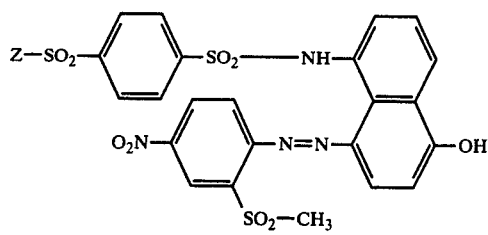
Compound B (magenta)
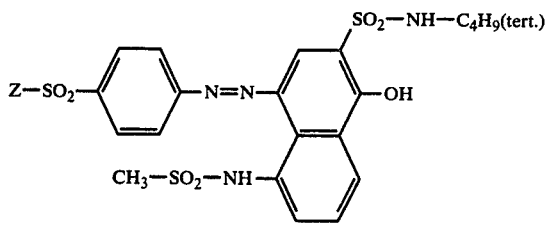
Compound C (yellow)
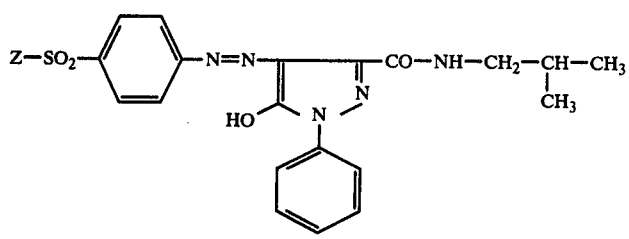
Compound D (magenta)
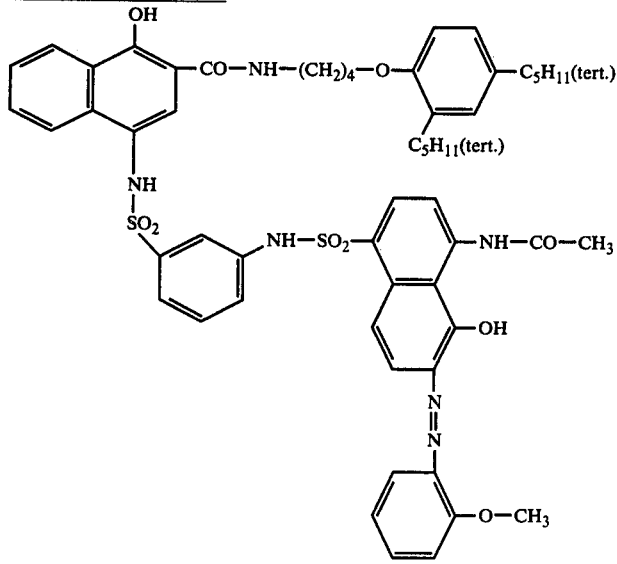
Compound E (Hardening agent)
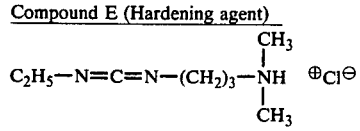

We claim:
1. A process for the production of direct-positive photographic images in which a photographic recording material having at least one light-sensitive silver halide emulsion layer which contains an unfogged direct-positive silver halide emulsion is exposed imagewise and developed in the presence of a fogging agent, wherein the improvement comprises the material contains from 0.1 to 100 mg per mol of silver halide of a fogging agent represented by the following general formula:

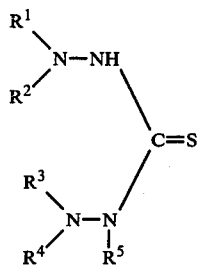

wherein
R$^1$ and R$^4$ are identical or different and represent hydrogen, a saturated or olefinically unsaturated aliphatic group, aryl, a heterocyclic group or acyl;
R$^2$ and R$^3$ are identical or different and represent hydrogen, a saturated or olefinically unsaturated aliphatic group, aryl or a heterocyclic group;
R$^5$ denotes hydrogen, and/or
R$^1$ together with R$^2$ and/or
R$^3$ together with R$^4$ represent a methylidene group optionally substituted by alkyl, aryl, a heterocyclic group or by acyl, wherein two such substituents together with the carbon atom of the methylidene group may complete a carbocyclic or heterocyclic ring; and/or
R$^1$ together with R$^4$ or R$^5$ represent the group required for completing a 5-membered or 6-membered heterocyclic ring selected from the group consisting of 1,2,3,4-tetrazolidine-5-thione, hexahydro-1,2,4,5-tetrazine-3-thione, hexahydro-1,2,4-triazine-3-thione and 2,3,4,5-tetrahydro-1,2,4-triazine-3-thione.

2. A light-sensitive photographic material for the production of direct-positive images having at least one light-sensitive silver halide emulsion layer which contains an unfogged direct-positive silver halide emulsion and comprising a fogging agent, wherein the improvement comprises the material contains from 0.1 to 100 mg per mol of silver halide of a fogging agent represented by the following general formula:

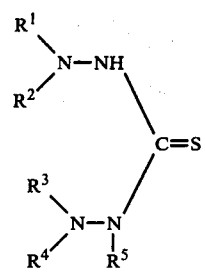

wherein
R$^1$ and R$^4$ are identical or different and represent hydrogen, a saturated or olefinically unsaturated aliphatic group, aryl, a heterocyclic group or acyl;
R$^2$ and R$^3$ are identical or different and represent hydrogen, a saturated or olefinically unsaturated aliphatic group, aryl or a heterocyclic group;
R$^5$ denotes hydrogen; and/or
R$^1$ together with R$^2$ and/or
R$^3$ together with R$^4$ represent a methylidene group which may be substituted by alkyl, aryl, a heterocyclic group or by acyl, and two such substituents together with the carbon atom of the methylidene group may complete a carbocyclic or heterocyclic ring; and/or
R$^1$ together with R$^4$ or R$^5$ denote the group required for completing a 5-membered or 6-membered heterocyclic ring selected from the group consisting of 1,2,3,4-tetrazolidine-5-thione, hexahydro-1,2,4,5-tetrazine-3-thione, hexahydro-1,2,4-triazine-3-thione and 2,3,4,5-tetrahydro-1,2,4-triazine-3-thione.

3. Material as claimed in claim 2, in which in the given formula, R$^1$ and/or R$^4$ denotes an acyl group which is derived from aliphatic or aromatic carboxylic or sulphonic acids.

4. Material as claimed in claim 2, in which in the given formula, R$^1$ together with R$^2$ and/or R$^3$ together with R$^4$ denote a methylidene group which forms part of a cyclopentane, cyclohexane, indane, indanone, indanedione, piperidine, pyrrolidone or indolone ring.

5. Material as claimed in claim 2, in which in the given formula at least one of R$^1$ and R$^4$ represents hydrogen.

6. Material as claimed in claim 2, which comprises in association with said light-sensitive silver halide emulsion layer a non-diffusible color providing compound which in its oxidized form is capable of releasing a diffusible dye under alkaline photographic development conditions.

* * * * *